(12) United States Patent
Dittes

(10) Patent No.: US 9,933,018 B2
(45) Date of Patent: Apr. 3, 2018

(54) BEARING WITH CONDITION MONITORING SENSOR

(71) Applicant: Nicholas Dittes, Sjulsmark (SE)

(72) Inventor: Nicholas Dittes, Sjulsmark (SE)

(73) Assignee: AKTIEBOLAGET SKF, Gothenburg (SE)

( * ) Notice: Subject to any disclaimer, the term of this patent is extended or adjusted under 35 U.S.C. 154(b) by 0 days.

(21) Appl. No.: 15/241,702

(22) Filed: Aug. 19, 2016

(65) Prior Publication Data

US 2017/0058956 A1    Mar. 2, 2017

(30) Foreign Application Priority Data

Aug. 26, 2015 (SE) .................................. 1551102

(51) Int. Cl.
| | | |
|---|---|---|
| *F16C 41/00* | (2006.01) | |
| *G01N 27/06* | (2006.01) | |
| *G01N 27/416* | (2006.01) | |
| *G01N 33/28* | (2006.01) | |
| *F16C 19/52* | (2006.01) | |
| *F16C 19/06* | (2006.01) | |
| *G01N 27/12* | (2006.01) | |

(52) U.S. Cl.
CPC .............. *F16C 41/00* (2013.01); *F16C 19/52* (2013.01); *F16C 19/525* (2013.01); *G01N 27/06* (2013.01); *G01N 27/4166* (2013.01); *G01N 33/2888* (2013.01); *F16C 19/06* (2013.01); *F16C 2202/32* (2013.01); *F16C 2233/00* (2013.01); *G01N 27/121* (2013.01)

(58) Field of Classification Search
CPC ........ F16C 19/52; F16C 19/525; F16C 41/00; F16C 41/002; G01N 27/048; G01N 27/121; G01N 27/4166; G01N 33/2888
See application file for complete search history.

(56) References Cited

U.S. PATENT DOCUMENTS

| | | | | |
|---|---|---|---|---|
| 4,792,791 A | * | 12/1988 | Cipris ................. | B60R 16/0234 340/438 |
| 5,184,505 A | * | 2/1993 | van den Berg ........ | G01N 33/30 73/10 |
| 6,546,785 B1 | * | 4/2003 | Discenzo ................ | F16C 19/52 137/805 |
| 2015/0355075 A1 | * | 12/2015 | Murray ............... | G01M 13/045 384/448 |

* cited by examiner

*Primary Examiner* — Phillip A Johnson
(74) *Attorney, Agent, or Firm* — Bryan Peckjian; SKF USA Inc. Patent Dept.

(57) ABSTRACT

A bearing arrangement is disclosed. The bearing arrangement includes a bearing with a bearing lubricant. A first electrically conductive portion and a second electrically conductive portion, which have different electronegativities, are in direct contact with the bearing lubricant. The bearing lubricant and the first and second electrically conductive portions form an electrolyte and two electrodes, respectively, of an electrochemical cell. The bearing arrangement further includes a sensor connected to the first electrically conductive portion and to the second electrically conductive portion, the sensor being configured to measure at least one of a current and a galvanic potential between the first and second electrically conductive portions and to determine a water content in the bearing lubricant based on the measurement.

6 Claims, 2 Drawing Sheets

BEARING WITH CONDITION MONITORING SENSOR

CROSS REFERENCE TO RELATED APPLICATIONS

This application claims priority to Swedish (SE) patent application no. 1551102-5 filed on Aug. 26, 2015, the contents of which are fully incorporated herein by reference.

FIELD OF THE INVENTION

The present invention relates to a bearing arrangement that includes a bearing and a sensor for monitoring the condition of the bearing.

BACKGROUND OF THE INVENTION

Bearings such as rolling bearings are used in all types of mechanical applications to reduce friction between moving parts. Rolling bearings provide low friction rotation by means of rolling elements arranged between an inner and an outer race. In order to reduce friction and wear between the rolling elements and the races, a bearing lubricant such as grease or oil is often used.

It has been found that bearing failures are often caused by water in the lubricant. Water in the lubricant can cause surface erosion and cavitations within the bearing as well as hydrogen embrittlement due to the extreme pressures in rolling element bearings. These may reach levels as high as 1 to 3 GPa, where water can disassociate into its constituent atoms. Free hydrogen atoms may then penetrate through the surfaces of the bearing components and make them brittle. Water also speeds up the oxidization of base oil and can cause additives to precipitate and form abrasive particles or sludge. Even in situations where there is no water entering the bearing from the outside, the water content in the lubricant may increase slightly due to oxidation of hydrocarbons in the lubricant.

The risk of unexpected bearing failures may be reduced by using a sensor that monitor the water content in the lubricant or some other parameter such as the temperature or pressure of the lubricant. Despite the efforts that have gone into developing such sensors, many of the systems that are currently available are often complicated and impractical to use in many application. There is thus a need for further development in this area.

BRIEF SUMMARY OF THE INVENTION

The object of the present invention is to provide an improved or alternative bearing arrangement that has a condition monitoring sensor, especially a sensor capable of providing information about the water content in the bearing lubricant.

According to a first aspect, a bearing arrangement is provided. The bearing arrangement comprises a bearing having an inner race, an outer race and several rolling elements arranged between the inner and outer races such that the inner race is rotatable relative to the outer race. The bearing arrangement also comprises a bearing lubricant arranged within the bearing to lubricate the rolling elements, a first electrically conductive portion and a second electrically conductive portion. The first and second electrically conductive portions have different electronegativity and are in direct contact with the bearing lubricant, whereby the bearing lubricant and the first and second electrically conductive portions form an electrolyte and two electrodes, respectively, of an electrochemical cell. The bearing arrangement further comprises a sensor connected to the first electrically conductive portion and to the second electrically conductive portion. The sensor is configured to measure at least one of a current and a galvanic potential between the first and second electrically conductive portions and to determine a degree of water content in the bearing lubricant based on the measurement.

The first and second portions (electrodes) are electrically isolated from each other except for mutual contact with the lubricant (electrolyte). The sensor connected to the first and second portions is therefore able to detect voltage and/or current generated by the electrochemical cell formed by these elements.

The invention is based on the realization that relevant information about the water content in the bearing lubricant can be obtained by measuring the current or voltage of an electrochemical cell which uses the bearing lubricant as its electrolyte. The electrodes of the electrochemical cell are here formed by the first and second electrically conductive portions, and these are made of two metals of different electronegativity, i.e. two metals having different ranks in the galvanic series such as zinc and steel. When a suitable electrolyte, in this case the bearing lubricant, is in contact with two such metals, a galvanic potential can be measured. It has been found that, as a general rule, the higher the water content in the bearing lubricant, the larger the galvanic potential between the first and second electrically conductive portions.

It has also been found that the impedance of the bearing lubricant is generally highest when the bearing lubricant is new and decreases with contamination. Information about the water content and other contaminants in the bearing lubricant can therefore be obtained by measuring the current running through the electrochemical cell. The impedance of the electrochemical cell is proportional to the condition of the bearing lubricant, and the higher the current through the electrochemical cell, the worse the condition will typically be. Oxidization inside the bearing can also reduce the impedance of the bearing lubricant, and measuring the current may therefore provide information about the rate of oxidization processes occurring inside the bearing.

The present invention makes it possible to make these voltage and current measurements in a very simple, reliable and energy-efficient way, without the need for post-processing of the measured data. Moreover, the components needed to perform the measurements are inexpensive and may be incorporated into existing bearing designs with only minor modifications thereto so that conventional production lines may, to a large extent, still be used.

One has significant freedom in choosing the positions of the first and second electrically conductive portions inside the bearing, something which makes the bearing arrangement very versatile and easy to adapt to a wide variety of applications. For example, in order to increase the chance of early detection of water in the bearing lubricant, one of the first and second electrically conductive portions may be arranged where water is more likely to accumulate, such as close to a side of the bearing arrangement that will be exposed to rain. Further examples of ways to arrange the first and second electrically conductive portions that may be particularly suitable for some applications follow below.

According to one embodiment, the first electrically conductive portion is the outer race. The outer race typically has a relatively large surface area in contact with the bearing lubricant and is therefore suitable as one of the first and second electrically conductive portions.

According to one embodiment, the bearing is arranged in a housing. The housing protects and seals the bearing from the environment. The housing typically has a relatively large surface area in contact with the bearing lubricant and is therefore suitable as one of the first and second electrically conductive portions.

According to one embodiment, the rolling elements are arranged between two plates, and the second electrically conductive portion is arranged on at least one of the plates. By arranging the second electrically conductive portion on both plates, it is possible to detect if the properties of the bearing lubricant are different on different sides of the bearing.

According to one embodiment, the second electrically conductive portion is a plating on at least one of the plates. Platings having the desired electrochemical properties are easy to make.

According to one embodiment, the second electrically conductive portion is a metal strip arranged on the outer race. Metal strips having the desired electrochemical properties are easy to make and also to integrate into bearings with stringent space restrictions.

According to one embodiment, the second electrically conductive portion is a metal strip arranged inside the housing.

BRIEF DESCRIPTION OF THE SEVERAL VIEWS OF THE DRAWING

This and other aspects of the present invention will now be described in more detail, with reference to the appended drawings showing embodiment(s) of the invention.

DETAILED DESCRIPTION OF THE INVENTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person.

Figure 1:
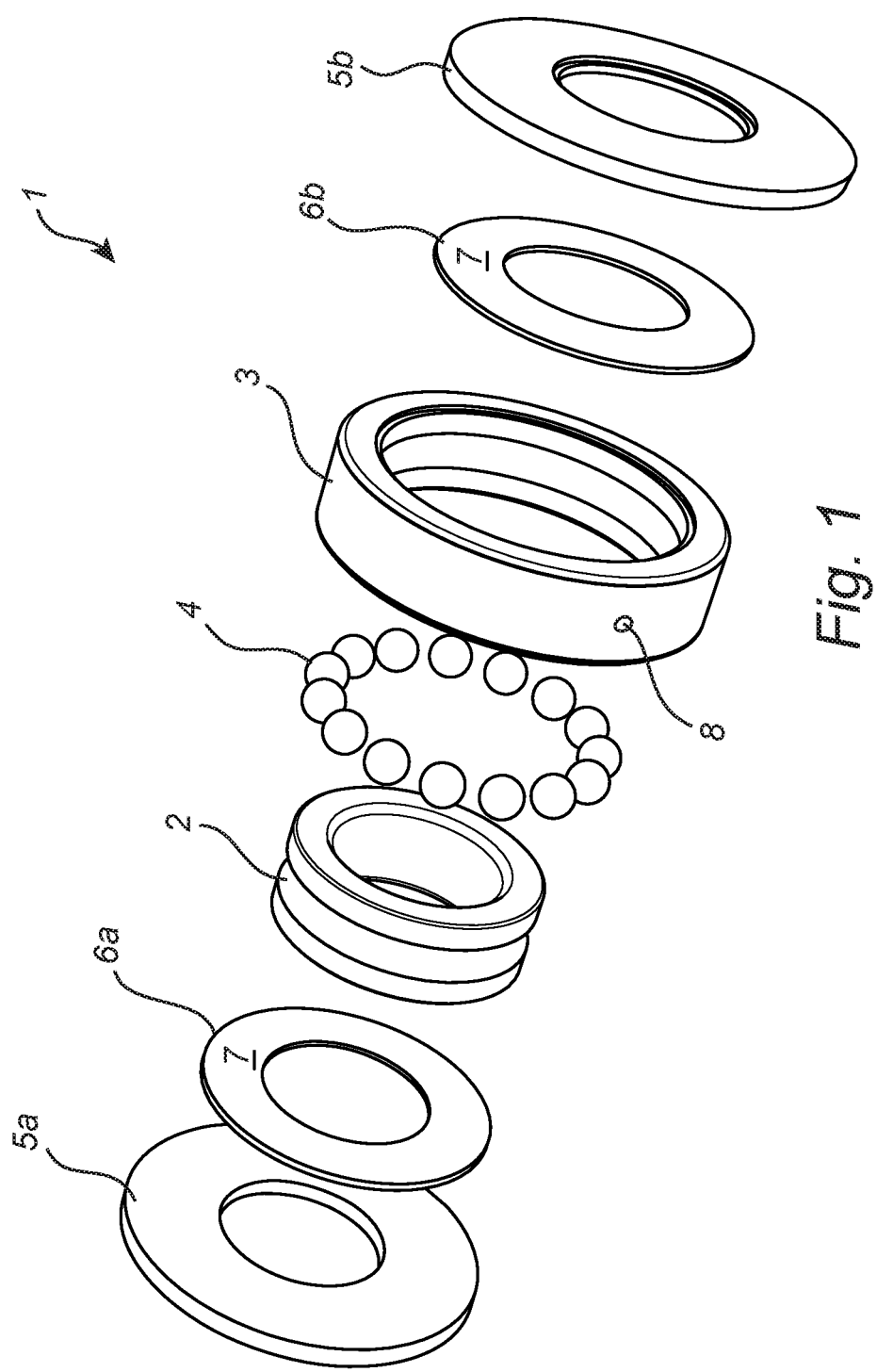
FIG. 1 shows a schematic exploded view of an embodiment of a bearing arrangement.

FIG. 1 shows a bearing arrangement 1 with a bearing that comprises an inner race 2 and an outer race 3 arranged coaxially with each other. Several rolling elements 4 in the form of balls are arranged between the inner and outer races 2, 3. A bearing lubricant (not shown) is arranged in the empty spaces between the inner and outer races 2, 3 so as to reduce friction between the rolling elements 4 and the inner and outer races 2, 3. The bearing lubricant will hereinafter be referred to as the "lubricant". The bearing further comprises sealing rings 5a, 5b arranged on respective sides of the rolling elements 4 and coaxially with the inner and outer races 2, 3. The sealing rings 5a, 5b seal the bearing and help to prevent the lubricant from leaking out. The sealing rings 5a, 5b, the races 2, 3 and the rolling elements 4 are made of steel. These components may in another example be made of some other metal, or metals, and all of them do not have to be made of the same material. The bearing may be provided with a cage for keeping the rolling elements 4 in place. Such cages are well known to the skilled person, and in order to avoid complicating the drawing no cage is shown in FIG. 1.

Two plates 6a, 6b are arranged coaxially with the inner and outer races 2, 3. The rolling elements 4 are arranged between the plates 6a, 6b. The plates 6a, 6b are made of steel but can be made of a different metal or a non-metallic material in other examples. Each of the plates 6a, 6b is provided with a plating 7 arranged so as to be in direct contact with the lubricant. The two platings 7 are made of a material that has a different electronegativity than the material of which the outer race 3 is made. The platings 7 may or may not be made of the same material. In this example, both of the platings 7 are zinc platings. The plates 6a, 6b may be completely or only partly covered by the platings 7. For example, only the sides of the plates 6a, 6b facing the rolling elements 4 may be provided with platings 7, or only a portion of those sides. A layer of an electrically isolating material, such as a plastic material, is arranged between the platings 7 and the plates 6a, 6b. Such a layer may be omitted in those examples where the plates 6a, 6b are not electrically conducting.

A sensor 8 is electrically connected to the outer race 3, which forms a first electrically conductive portion, and to the platings 7 which form a second electrically conductive portion. The sensor 8 is adapted to measure a galvanic potential between the outer race 3 and each of the platings 7 and/or a current flowing through the lubricant between the outer race 3 and the platings 7. The sensor 8 may be configured to transmit the results of such measurements to an external hardware unit, via a wired connection and/or via a wireless connection. The sensor 8 is here integrated with the outer race 3 but may be arranged differently in another example.

It should be noted that it is possible to omit one or both of the plates 6a, 6b and to have, for instance, one or more metal strips form the second portion instead of the platings 7. Such metal strips may for example be arranged on the outer race 3, with an electrically isolating layer interposed therebetween.

It should also be noted that the sensor 8 may in other examples be adapted to also measure the capacitance of the lubricant. Such capacitance measurements may yield additional information about the condition of the lubricant and are described in the international patent application, with application number PCT/SE2015/050544, hereby incorporated by reference. In short, the bearing arrangement should then be modified so that the sealing rings 5a, 5b form a parallel plate capacitor with the lubricant as the dielectric.

Figure 2:
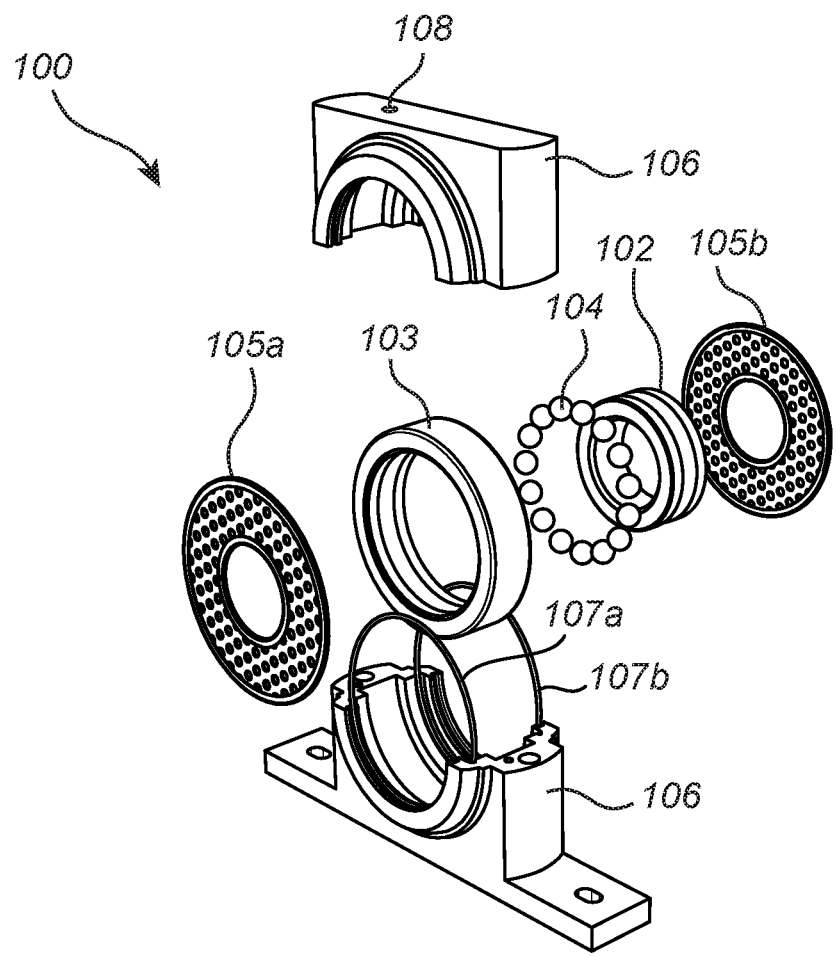
FIG. 2 shows a schematic exploded view of another embodiment of a bearing arrangement.

FIG. 2 shows a bearing arrangement 100 with a bearing that comprises an inner race 102 and an outer race 103 which are arranged coaxially with each other. Several rolling elements 104 in the form of balls are arranged between the inner and outer races 102, 103. The bearing may be provided with a cage for keeping the rolling elements 104 in place. Such cages are well known to the skilled person, and in order to avoid complicating the drawing no cage is shown in FIG. 2. The bearing further comprises perforated plates 105a, 105b arranged on respective sides of the rolling elements 104 and coaxially with the inner and outer races 102, 103. It should be noted that the perforated plates 105a, 105b are optional and may be omitted in another example. The perforated plates 105a, 105b, the rolling elements 104 and the inner and outer races 102, 103 are arranged inside a housing 106. A bearing lubricant (not shown) for lubricating the rolling elements 104 is arranged in the empty spaces inside the housing 106. The bearing lubricant will hereinafter be referred to as the "lubricant". The perforations in the perforated plates 105a, 105b allow the lubricant to flow there through. The housing 106, the perforated plates 105a, 105b, the rolling elements 104 and the inner and outer races 102, 103 are made of steel. These components may in another example be made of some other metal, or metals, and all of them do not have to be made of the same material.

Two metal strips 107a, 107b (hereinafter referred to as "strips") are arranged inside the housing 106 so as to be in direct contact with the lubricant. In this example, the strips 107a, 107b are circular and the housing 106 has two grooves in which the strips 107a, 107b are positioned. An electrically isolating layer is arranged between the strips 107a, 107b and the housing 106. The strips 107a, 107b are coaxial with the inner and outer races 102, 103, and the rolling elements 104 are arranged between the strips 107a, 107b. There are of course other ways to arrange one, two or more strips inside the housing 106. For example, one strip may be arranged on the outer race 103, with an electrically isolating layer interposed therebetween. The strips 107a, 107b are made of a material that has a different electronegativity than the material of which the housing 106 is made. The strips 107a, 107b may or may not be made of the same material. In this example, both of the strips 107a, 107b are made of zinc.

A sensor 108 is electrically connected to the housing 106, which forms a first electrically conductive portion, and to the strips 107a, 107b which form a second electrically conductive portion. The sensor 108 is adapted to measure a galvanic potential between the housing 106 and each of the strips 107a, 107b and/or a current flowing through the lubricant between the housing 106 and each of the strips 107a, 107b. The sensor 108 may be configured to transmit the results of such measurements to an external hardware unit, via a wired connection and/or via a wireless connection. The sensor 108 is here integrated with the housing 106 but may be arranged differently in another example.

It should be noted that it is possible to omit the strips 107a, 107b and to have the perforated plates 105a, 105b form the second electrically conductive portion instead. The perforated plates 105a, 105b may for example be provided with platings similarly to the plates 6a, 6b of the bearing arrangement 1 in FIG. 1.

It should be noted also that the sensor 108 may in another example be adapted to also measure the capacitance of the lubricant. Such capacitance measurements may yield additional information about the condition of the lubricant and are described in the international patent application, with application number PCT/SE2015/050544. In short, the bearing arrangement 100 should then be modified so that the perforated plates 105a, 105b form a parallel plate capacitor with the lubricant as the dielectric.

An outline of how the condition of the lubricant may be monitored is given next with reference to FIGS. 1 and 2. The monitoring is based on the fact that the first electrically conductive portion and the second electrically conductive portion are arranged so as to form a respective electrode of an electrochemical cell which uses the lubricant as its electrolyte. The sensor 8, 108, which may operate while the bearing is rotating as well as while the bearing is not rotating, first measures a galvanic potential, i.e. a voltage difference, between the first and second electrically conductive portions and/or a current flowing between these portions through the lubricant. The sensor 8, 108 may be adapted to perform these measurements continuously and/or on demand. The value obtained from the measurement is then compared with a reference value. The reference value may be a value of a previous measurement on the same device under similar conditions, such as the most recently measured value prior to the current measurement. Alternatively, the reference value may be a value of a measurement on a similar device or a theoretically calculated value. A reference value for the galvanic potential may be based on the known electronegativities of metals. Any difference between the measured value and the reference value is usually compared with a threshold value to rule out variations due to for example measurement inaccuracies. If the detected difference between the measured value and the reference value is larger than the threshold value, the properties of the lubricant may have changed in a way that is detrimental to the performance of the bearing or that leads to an increased risk of bearing failure. In particular, any increase in the galvanic potential and/or in the current usually means that the water content in the lubricant has increased.

The person skilled in the art realizes that the present invention by no means is limited to the embodiments described above. The present invention is in fact applicable to virtually any type of lubricated bearing so many modifications and variations are possible within the scope of the appended claims. For example, although the embodiments discussed herein relate to ball bearings, the rolling elements 4, 104 do not have to be balls but may be cylindrical or conical, for instance.

The invention claimed is:

1. A bearing arrangement comprising:
   a bearing having an inner race, an outer race and a plurality of rolling elements arranged between the inner and outer races such that the inner race is rotatable relative to the outer race;
   a bearing lubricant arranged within the bearing to lubricate the rolling elements;
   a first electrically conductive portion and a second electrically conductive portion, the first and second electrically conductive portions having different electronegativity and being in direct contact with the bearing lubricant, so that the bearing lubricant and the first and second electrically conductive portions form an electrolyte and two electrodes, respectively, of an electrochemical cell; and
   a sensor connected to the first electrically conductive portion and to the second electrically conductive portion, the sensor being configured to measure at least one of a current and a galvanic potential between the first and second electrically conductive portions and to determine a water content in the bearing lubricant based on the measurement,
   wherein the rolling elements are arranged between two plates, and wherein the second electrically conductive portion is arranged on at least one of the plates.

2. The bearing arrangement according to claim 1, wherein the first electrically conductive portion is the outer race.

3. The bearing arrangement according to claim 1, wherein the bearing is arranged in a housing.

4. The bearing arrangement according to claim 1, wherein the second electrically conductive portion is a plating on at least one of the plates.

5. A bearing arrangement comprising:
   a bearing having an inner race, an outer race and a plurality of rolling elements arranged between the inner and outer races such that the inner race is rotatable relative to the outer race;
   a bearing lubricant arranged within the bearing to lubricate the rolling elements;

a first electrically conductive portion and a second electrically conductive portion, the first and second electrically conductive portions having different electronegativity and being in direct contact with the bearing lubricant, so that the bearing lubricant and the first and second electrically conductive portions form an electrolyte and two electrodes, respectively, of an electrochemical cell; and a sensor connected to the first electrically conductive portion and to the second electrically conductive portion, the sensor being configured to measure at least one of a current and a galvanic potential between the first and second electrically conductive portions and to determine a water content in the bearing lubricant based on the measurement, wherein the second electrically conductive portion is a metal strip arranged on the outer race.

6. A bearing arrangement comprising:

a bearing having an inner race, an outer race and a plurality of rolling elements arranged between the inner and outer races such that the inner race is rotatable relative to the outer race;

a bearing lubricant arranged within the bearing to lubricate the rolling elements;

a first electrically conductive portion and a second electrically conductive portion, the first and second electrically conductive portions having different electronegativity and being in direct contact with the bearing lubricant, so that the bearing lubricant and the first and second electrically conductive portions form an electrolyte and two electrodes, respectively, of an electrochemical cell; and a sensor connected to the first electrically conductive portion and to the second electrically conductive portion, the sensor being configured to measure at least one of a current and a galvanic potential between the first and second electrically conductive portions and to determine a water content in the bearing lubricant based on the measurement, wherein the second electrically conductive portion is a metal strip arranged inside the housing.

* * * * *